United States Patent
Abe et al.

(10) Patent No.: US 6,224,861 B1
(45) Date of Patent: *May 1, 2001

(54) AMINO ACID COMPOSITION

(75) Inventors: Takashi Abe, Wako; Hiroshi Tsuchita, Hoya; Koji Iida, Tokyo, all of (JP)

(73) Assignees: The Institute of Physical and Chemical Research., Wako; Meiji Milk Products Co., Ltd., Tokyo, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/112,354

(22) Filed: Jul. 9, 1998

Related U.S. Application Data

(63) Continuation of application No. PCT/JP97/00028, filed on Jan. 9, 1997.

(30) Foreign Application Priority Data

Jan. 9, 1996 (JP) .................................................... 8-001547

(51) Int. Cl.$^7$ ........................ A61K 38/48; A61K 31/415; A61K 31/195
(52) U.S. Cl. ...................... 424/94.64; 514/400; 514/561; 514/565
(58) Field of Search ........................ 424/94.64; 514/561, 514/400, 565

(56) References Cited

FOREIGN PATENT DOCUMENTS

| 3-128318 | 5/1991 | (JP) . |
| 4-120020 | 1/1992 | (JP) . |
| 4-95026 | 3/1992 | (JP) . |
| 8-198748 | 8/1996 | (JP) . |

OTHER PUBLICATIONS

Hiroshi Tsuchita, et al., Database Chemabs, Chemical Abstracts Service, AN 127:16965, vol. 17, No. 6, "Effects of a Vespa Amino Acid Mixture Identical to Hornet Larval Saliva on the Blood Biochemical Indices of Running Rats", 1997.

Takashi Abe, Database Chemabs, Chemical Abstracts Service, AN 122:287556, vol. 16, No. 1, "Effect of Vespa Amino Acid Mixture from Hornet Larval Saliva on Endurance Exercise", 1995.

Takashi Abe, et al., Database Biosis, Biosciences Information Service, AN 1995:340637, vol. 44, No. 2, "Effects of Vespa Amino Acid Mixture (VAAM) Isolated from Hornet Larval Saliva and Modified VAAM on Endurance Exercise in Swimming Mice: Improvement in Performance and Changes of Blood Lactate and Glucose", 1995.

Hiromichi Kobayashi et al., "Oral Amino Acid Compositions Promoting Recovery from Physical and Metal Fatigue", Chemical Abstracts, vol. 125, No. 17, 125:220495e, 1996. Corresponds with JP 8–198748 listed above.

Susan M. Garthwaite et al., "Increased Permeability to Sugar Following Muscle Contraction", The Journal of Biological Chemistry, Vol 257, No. 9, May 10, 1992, pp. 5008–5012.

*Primary Examiner*—Raymond Henley, III
(74) *Attorney, Agent, or Firm*—Oblon, Spivak, McClelland, Maier & Neustadt, P.C.

(57) ABSTRACT

An amino acid composition comprising the following amino acids at the following molar ratio: proline (12.6 to 23.4), alanine (8.4 to 15.6), glycine (13.3 to 24.9), valine (8.2 to 15.4), threonine (5.0 to 9.4), eucine (4.3 to 8.1), histidine (1.8 to 11.9), serine (1.7 to 3.3), lysine (6.0 to 11.2), isoleucine (3.1 to 5.9), glutamic acid (2.2 to 10.4), arginine (2.4 to 4.6), phenylalanine (2.6 to 5.0), tyrosine (4.2 to 7.8) and trypsin (1.5 to 2.9). The composition supplements blood amino acids reduced during hard exercise and shows effects to improve motor function, to reduce fatigue after exercise and to help recovery from the fatigue.

8 Claims, 12 Drawing Sheets

AMINO ACID COMPOSITION

This is a continuation of PCT/JP97/00028 filed Jan. 9, 1997.

TECHNICAL FIELD

This invention relates to an amino acid composition prepared based on the knowledge about amino acid components found in hornet (Vespa mandalinia) larval saliva. More particularly, this invention relates to an amino acid composition which supplements blood amino acids reduced during hard exercise and which could improve motor function, reduce exhaustion after exercise and help recovery from fatigue and a supplementary liquid comprising such amino acid composition.

PRIOR ART

There have been little reports on larvae of the hornet, in particular, on the larval saliva of the hornet. Thus, a composition of the larval saliva of the hornet has never been elucidated. There has been no knowledge about what nutrients provide sufficient energy for marvelous muscle endurance of the hornet.

The inventors of this invention have studied larval saliva of various kinds of hornets and determined a composition of the saliva. As a result, they have found that the saliva has an effect to control lipid and carbohydrate metabolism and elucidated the effect ingredients of the saliva. They have also found that an amino acid nutritient liquid secreted by the larval hornet controls the metabolism of lipid and carbohydrate during exercise when it is orally administered (see, for example, JP-A-3-128318, JP-A-4-95026, JP-A-4-112825 and JP-A-4-120020).

The inventors have already found that the hornet nutrient liquid restrains the formation of fatigue substances and prevents the reduction of blood sugar level during exercise and increases the motor function. They have also found that the mechanism of the action is in that the liquid accelerates the utilization of lipid to provide energy for exercise. It has bee suggested that VAAM (Vespa Amino Acid Mixture), a main ingredient of the nutrient liquid would have various effects such as recovery from fatigue during exercise in addition to the actions mentioned above.

On the other hand, it has also been known that blood amino acid balance is significantly lost by exercise fatigue. It is believed that this is resulted from wear and breakdown of body tissues by the stress during exercise. However, so far, no attention has been paid to physiological meaning and significance of such lost of blood amino acid balance.

The inventors of the present invention have farther studied the relationship between the amino acid composition of the VAAM and blood amino acid levels after exercise. As a result, they have found that the amino acid composition of the VAAM has very high correlation with the blood amino acid levels which are reduced according to fatigue after exercise. Namely, the higher the reduction of an amino acid level in blood due to fatigue, the higher the level of the amino acid in the VAAM.

Accordingly, it is believed that supplement of these amino acids would be essential for improvement of motor function and recovery from fatigue. As described above, the present invention has been completed based on the finding that human blood amino acid level reduced by exercise fatigue has very high correlation with the amino acid composition of the VAAM.

DISCLOSURE OF THE INVENTION

An object of the present invention is to provide an amino acid composition which supplements blood amino acids which are reduced during hard exercise and has the ability to increase motor function, to reduce fatigue and to help recovery from fatigue, in particular a supplementary liquid.

Another object of the present invention is to provide a method which restrains the variation of blood amino acid levels during hard exercise to keep the blood amino acid level constant, and an amino acid composition which is used in the method, in particular a supplementary liquid.

The present invention provides an amino add composition comprising the following amino acids at the molar ratio indicated below hereinafter the composition may also be referred to as HVAAM).

| | |
|---|---|
| Proline | 12.6 to 23.4 moles |
| Alanine | 8.4 to 15.6 moles |
| glycine | 13.3 to 24.9 moles |
| valine | 8.2 to 15.4 moles |
| threonine | 5.0 to 9.4 moles |
| leucine | 4.3 to 8.1 moles |
| histidine | 1.8 to 11.9 moles |
| serine | 1.7 to 3.3 moles |
| lysine | 6.0 to 11.2 moles |
| isoleucine | 3.1 to 5.9 moles |
| glutamic acid | 2.2 to 10.4 moles |
| arginine | 2.4 to 4.6 moles |
| phenylalanine | 2.6 to 5.0 moles |
| tyrosine | 4.2 to 7.8 moles |
| and | |
| trypsin | 1.5 to 2.9 moles. |

The present invention also provides a method for restraining the change in blood amino acid levels during exercise, which comprises administering HVAAM to a mammal.

Further, the present invention provides an amino acid composition for a restraining the change in blood amino acid levels during exercise, which comprises amino acids in molar ratio equal to that in the VAAM, or between ±30% of the ratio in the VAAM (that is, between 30% greater than the ratio in the VAAM and 30% lower than the ratio in the VAAM, preferably ±20% of the ratio in the VAAM, more preferably ±10% of the ratio in the VAAM, that is, an amino acid composition comprising the following amino acids at the following molar ratio. Hereinafter, the amino acid compositions may also be generically named as "VAAM". The invention also provides a method for restraining the change in blood amino acid levels during exercise, which comprises administering the amino acid composition to a mammal.

| | |
|---|---|
| Proline | 12.6 to 23.4 moles |
| Alanine | 4.2 to 7.8 moles |
| Glycine | 13.3 to 24.9 moles |
| Valine | 4.1 to 7.7 moles |
| Threonine | 5.0 to 9.4 moles |
| Leucine | 4.3 to 8.1 moles |
| Histidine | 1.8 to 3.8 moles |
| Serine | 1.7 to 3.3 moles |
| Lysine | 6.0 to 11.2 moles |
| Isoleucine | 3.1 to 5.9 moles |
| glutamic acid | 2.2 to 4.2 moles |
| arginine | 2.4 to 4.6 moles |
| phenylalanine | 2.6 to 5.0 moles |
| tyrosine | 4.2 to 7.8 moles |
| trypsin | 1.5 to 2.9 moles |

The present invention also relates to use of HVAAM for the preparation of an amino acid composition which can supplement blood amino acids reduced during hard exercise to improve motor function, to reduce the fatigue after exercise and to help recovery from the fatigue; use of VAAM for the preparation of an amino acid composition which can supplement blood amino acids reduced during hard exercise to improve motor function, to reduce the fatigue after exercise and to help recovery from the fatigue; use of HVAAM for the preparation of an amino acid composition which can restrain the change in blood amino acid levels to keep the levels constant; and, use of VAAM for the preparation of an amino acid composition which can restrain the change in blood amino acid levels to keep the levels constant.

BEST MODES FOR CARRYING OUT THE INVENTION

Figure 1:
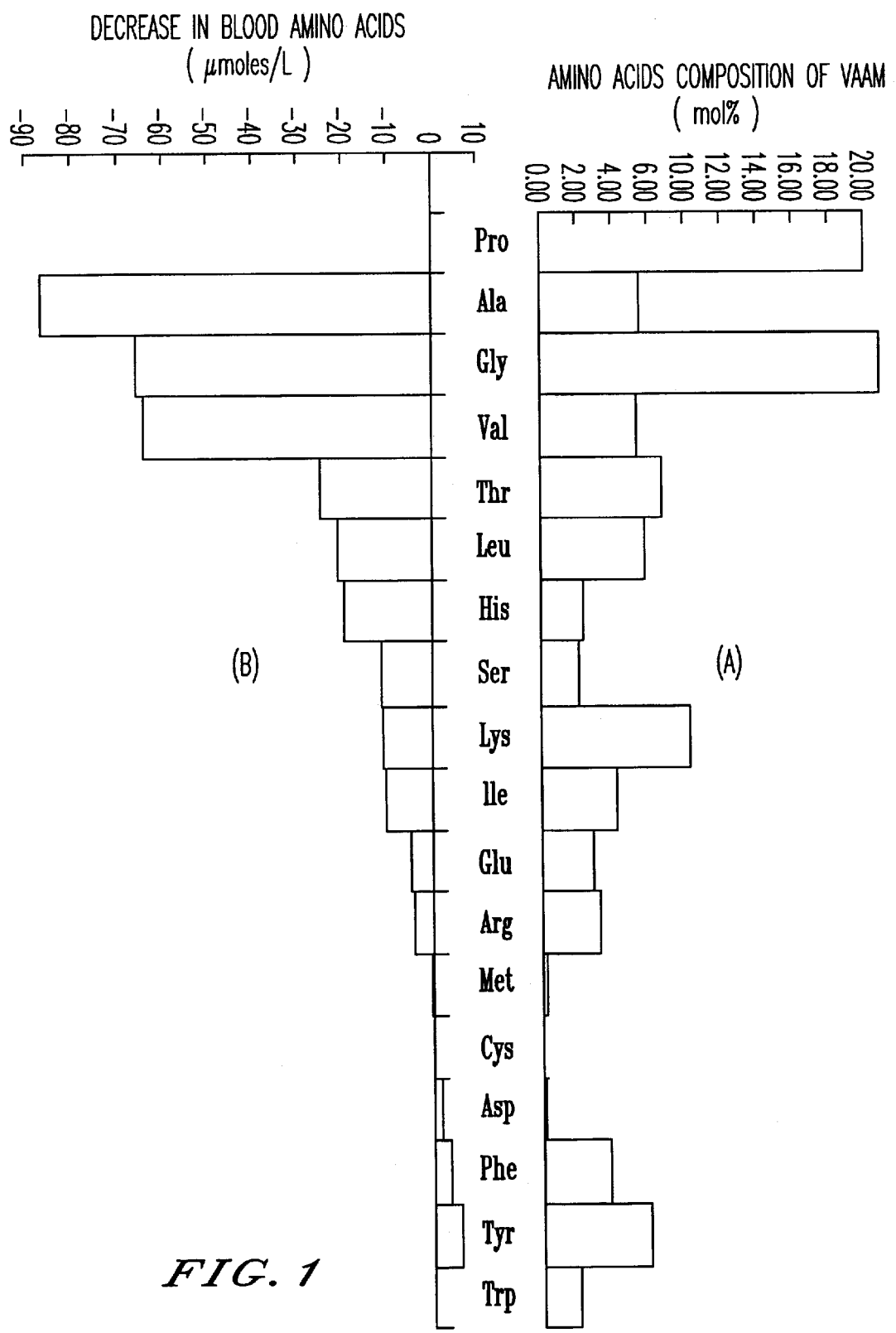
FIG. 1 shows a relationship between the amino aced composition in the VAAM (mole %) (A) and the decrease in blood amino acid levels during exercise fatigue ($\mu$moles/L) (B).

The amino acid composition (HVAAM) of the preferred embodiment of the invention comprises the following amino acids at the indicated molar ratio.

| ratio. | |
|---|---|
| Proline | 14.4 to 21.6 moles |
| Alanine | 9.6 to 14.4 moles |
| Glycine | 15.2 to 23.0 moles |
| Valine | 9.4 to 14.2 moles |
| Threonine | 5.8 to 8.7 moles |
| Leucine | 5.0 to 7.5 moles |
| Histidine | 2.0 to 11.0 moles |
| Serine | 2.0 to 3.0 moles |
| Lysine | 6.8 to 10.4 moles |
| Isoleucine | 3.6 to 5.4 moles |
| glutamic acid | 2.5 to 9.6 moles |
| arginine | 2.8 to 4.2 moles |
| phenylalanine | 3.0 to 4.6 moles |
| tyrosine | 4.6 to 7.2 moles |
| trypsin | 1.7 to 2.7 moles |

The amino acid composition (HVAAM) of the more preferred embodiment of the invention comprises the following amino acids at the indicated molar ratio.

| Proline | 16.2 to 19.8 moles |
|---|---|
| Alanine | 10.8 to 13.2 moles |
| Glycine | 17.1 to 21.1 moles |
| Valine | 10.6 to 13.0 moles |
| Threonine | 6.4 to 8.0 moles |
| Leucine | 5.5 to 6.8 moles |
| Histidine | 2.3 to 10.1 moles |

-continued

| | |
|---|---|
| Serine | 2.2 to 2.8 moles |
| Lysine | 7.7 to 9.5 moles |
| Isoleucine | 4.0 to 5.0 moles |
| glutamic acid | 2.8 to 8.8 moles |
| arginine | 3.1 to 3.9 moles |
| phenylalanine | 3.4 to 4.2 moles |
| tyrosine | 5.4 to 6.6 moles |
| trypsin | 1.9 to 2.5 moles |

In the composition of the present invention (HVAAM) the molar ratio of histidine is preferably 6.4 to 11.9 moles, more preferably 7.2 to 11.0 moles and most preferably 8.1 to 10.1 moles, and that of glutamic acid is preferably 5.6 to 10.4 moles, more preferably 6.4 to 9.6 moles and most preferably 7.2 to 8.8 moles.

Amino acids used in the amino acid composition of the present invention are preferably L-amino acids. The amino acid composition of the present invention may comprise, in addition to the a no acids mentioned above, methionine preferably 0.3 to 0.7 mole %, more preferably 0.4 to 0.6 mole %), aspartic acid (preferably 0.1 to 0.3 mole %), taurine (Tau) preferably 3 mole % or less), phosphoric acid ethanolamine (P-EtAm) (preferably 2 mole % or less), cystine (Cys) preferably 0.5 mole % or less), β-alanine (β-Ala) (preferably 1 mole % or less), γ-amino butyric acid (GABA) (preferably 0.5 mole % or less), ornithine (Orn) or ethanolamine (EtAm) (preferably 3 mole % or less), ammonia ($NH_3$) preferably 2 mole % or less), 1-methyl histidine (1-MeHis) (preferably 3 mole % or less), and -methyl histidine (3-MeHis) (preferably 1 mole % or less).

The amino acid composition of the present invention may easily prepared by mixing the above-mentioned amino acids which are commercially available at the above-mentioned ratio. The supplementary liquid of the present invention may easily be prepare by dissolving the amino acid composition in distilled water. The amino acid composition of the present invention may usually be in the form of powder for convenience, and be dissolved in distilled water when necessary. Temperature at which the composition of the invention is prepared or stored is not limited to specific one but preferably a room temperature or below. The composition of the invention is bitter a little but does not show toxicity at all when it is orally administered to mice at the dose of 20 g/kg. It has $LD_{50}$ of much higher than 20 g/kg.

The amino acid composition of the present invention is useful as a medicine or foods such as beverages. If it is used as a medicine, dosage forms are not limited to specific ones and it can be administered in the form of conventional administration such as oral or rectal administration, or other administration such as injection and infusion. If it is orally administered, it may be in the form of a composition having the above formulation or in the form of such formulations as tablets, capsules, powder, troche, and syrups with pharmaceutically acceptable carrier or excipient. However, solid formulations such as tablets and powders sometimes are hard to be adsorbed. Accordingly, oral administration in the form of for example liquid forms is preferred. In that case, it is preferably administered in the form of an aqueous solution comprising the amino acids and appropriate additives such as salts (e.g., sodium chloride), buffers, chelating agent. Injections may be prepared by adding appropriate buffers or isotonizing agents to the amino acid composition and dissolving them in sterilized distilled water, and they may be administered through intravenous drip infusion If it is used as foods, an appropriate flavor may be added to prepare drinkable preparations such as refreshing beverages, powdered drinks (e.g., encapsulated powders prepared by spray drying method, freeze drying method, or microfine powder method), or tablets.

The composition of the present invention is very low toxic and dose amounts may vary widely. Dose amounts vary depending on administration methods and purposes, and the amounts usually are in the range of from 1 to 12 g/dose, and from 3 to 18 g/day, preferably 2 to 4 g/dose, and from 6 to 12 g/day, as a solid content of the amino acid composition.

If it is used as a supplementary liquid for before, during or after exercise, it is administered one to three times a day in the amount of from 200 to 500 ml per day, as 0.8 to 1.5% by weight solution. If it is used as injection, it is administered in the amount of from 100 1 400 ml, preferably from 150 to 300 ml per dose as 0.8 to 1.5% by weight solution.

EXAMPLES

The present invention will now be explained in d tail with reference to test examples and formulation examples to which the present invention is not limited.

Test Example 1

(Running test in human)

This test was conducted to examine the change in the composition of blood amino acids before and after running in human.

(1) Quantitative analysis of blood amino acids

A blood sample (0.1 ml) was taken, to which the same amount of 1N perchloric acid was added to denature proteins and centrifuged. The supernatant (50 μl) was taken, to which one ml of a sample diluter for amino acid analysis was added to prepare a sample for the analysis. Amino acid analyzer HITACHI 835) and ninhydrin reaction were used.

(2) Test in human

Test subjects were subjected to running for 90 minutes on a treadmill under the load of 70% $VO_2$max (70% of the maximum oxygen intake) at room temperature (24° C.) and then they were subjected to bicycle ergometer exercise for 90 minutes. Bloods were taken before and after the exercise and examined for the concentration of amino acids. The results are shown in Table 1.

TABLE 1

| | Concentration of amino acid (μmole/l) | | | |
|---|---|---|---|---|
| Amino acids | Before exercise (A) | After exercise (B) | Decrease (A − B) | Decrease [(A − B)/A] × 100 |
| Pro | 160.70 | | | |
| Ala ** | 309.50 | 222.50 | 87.00 | 28.11 |
| Gly ** | 206.20 | 140.20 | 66.00 | 32.01 |
| Val ** | 214.50 | 150.00 | 64.50 | 30.07 |
| Thr ** | 130.70 | 106.10 | 24.60 | 18.82 |
| Leu ** | 114.00 | 92.40 | 21.60 | 18.95 |
| His ** | 62.40 | 42.00 | 20.40 | 32.70 |
| Ser ** | 113.40 | 101.10 | 12.30 | 10.85 |
| Lys | 147.90 | 135.90 | 12.00 | 8.11 |
| Ile ** | 67.00 | 55.30 | 11.70 | 17.46 |
| Glu ** | 22.40 | 16.10 | 6.30 | 28.13 |
| Arg | 63.80 | 57.80 | 6.00 | 9.40 |
| Met | 24.90 | 23.40 | 1.50 | 6.02 |
| Cys | 43.70 | 43.10 | 0.60 | 1.37 |
| Asp | 2.80 | 4.30 | −1.50 | −53.57 |
| Phe | 45.60 | 48.60 | −3.00 | −6.58 |
| Tyr | 53.90 | 59.90 | −6.00 | −11.13 |
| Trp | 36.80 | | | |

Correlation between change in blood amino acids by exercise and amino acid composition of the VAAM There were observed three groups of amino acids in terms of blood concentrations after exercise, a first group wherein blood concentration significantly decreased, a second one wherein blood concentration did not change very much, and a third one wherein blood concentration slightly increased Amino acids which decreased with significant difference (0.05<p) (** was added) are alanine, glycine, valine, threonine, leucine, histidine, serine, isoleucine, glutamic acid, etc. Tyrosine increased with significant difference. Phenylalanine and aspartic acid increased without significant difference. Lysine, arginine, methionine cystine and tryptophan decreased without significant difference. Among them, the amino acids which decreased with significant difference are those having high levels in the VAAM (see FIG. 1). In FIG. 1, A represents amino acid components (mole %) and B the decrease in blood amino acid concentration ($\mu$mole/l) after exercise shown in Table 1.

The results show the usefulness of the VAAM as an amino acid composition for exercise.

Example 1

Figure 2:
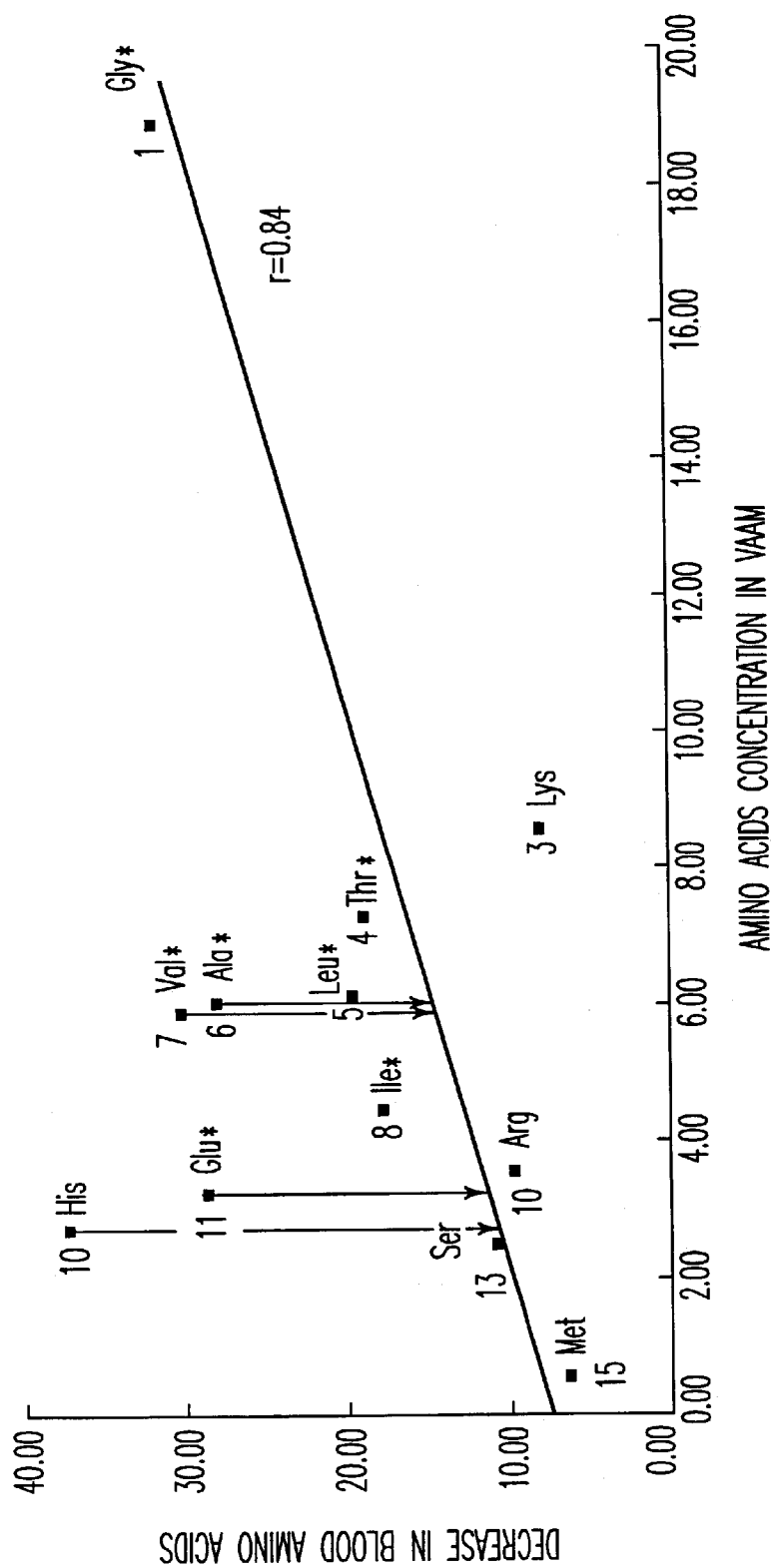
FIG. 2 shows a correlation between the decrease in blood amino acid levels (%) caused by exercise fatigue and the amino acid content in the VAAM (mole %) as shown in FIG. 1. Numerals in the figure are in the order of from the highest amino acid content in the VAAM and the amino acids to which the signal (*) is added show significant decrease.

Preparation of human amino acid composition based on the correlation between change in blood amino acids by exercise and amino acid composition of the VAAM, and the effects of the preparation As FIG. 1 suggests, the concentration (A) of alanine and valine in the VAAM are lower than the decrease (B) in human after exercise. On the other hand, histidine and glutamic acid do not have any effect on lipid induction, which was previously reported. Taking these points into account, the decrease (%) in blood concentration of each amino acid after exercise was plotted against molar ratio of the amino acid in the VAAM to give FIG. 2. FIG. 2 shows that the decrease (%) in blood amino acids after exercise approximately correlates with molar ratio of the amino acids in the VAAM (r =0.84). The results strongly suggest the usefulness of the VAAM during exercise. However, as seen from FIG. 2, alanine, valine, histidine and glutamic acid are decreased significantly coming away from the correlation regression line. It is therefore expected that the increase of these amino acid contents in the VAAM to meet the correlation would make an amino acid composition having much more excellent ability to improve motor function and to help recovery from fatigue than the VAAM.

The decrease of histidine, glutamic acid, valine alanine is 3.5, 2.5, 2.0 and 2.0 times, respectively, as large as that expected from the correlation regression line of FIG. 2. The amino acid composition of the present invention is prepared by increasing the contents of these four amino acids in an amino acid composition having the same ammo acid composition of the VAAM The addition of these amino acids makes the a no acid composition more suitable for motor function and recovery from fatigue in human. One example (HVAAMA) of such amino acid compositions (HVAAM) is shown in Table 2.

Further, since histidine and glutamic acid are relatively low in content and effect of lipid induction, it is possible to obtain the intended objects without the addition of these two amino acids. One example (HVAAMB) of such amino acid compositions is also shown in Table 2 In fact, oral administration of 300 ml of 1.5% by weight aqueous solution of the amino acid compositions A and B in Table 2 after exercise significantly improved a sense of fatigue and muscle pain after exercise.

TABLE 2

| Amino acid | Amino acid concentration (molar ratio) | | | |
|---|---|---|---|---|
| | VAAM | HVAAMA | HVAAMB | CAAM |
| Pro | 18.00 | 18.00 | 18.00 | 8.50 |
| Ala | 6.00 | 12.00 | 12.00 | 4.50 |
| Gly | 19.10 | 19.10 | 19.10 | 4.50 |
| Val | 5.90 | 11.80 | 11.80 | 5.50 |
| Thr | 7.20 | 7.20 | 7.20 | 2.50 |
| Leu | 6.20 | 6.20 | 6.20 | 8.50 |
| His | 2.60 | 9.10 | 2.60 | 2.50 |
| Ser | 2.50 | 2.50 | 2.50 | 8.00 |
| Lys | 8.60 | 8.60 | 8.60 | 7.00 |
| Ile | 4.50 | 4.50 | 4.50 | 5.50 |
| Glu | 3.20 | 8.00 | 3.20 | 19.60 |
| Arg | 3.50 | 3.50 | 3.50 | 3.00 |
| Met | 0.50 | 0.50 | 0.50 | 2.50 |
| Asp | 0.20 | 0.20 | 0.20 | 7.50 |
| Phe | 3.80 | 3.80 | 3.80 | 4.00 |
| Tyr | 6.00 | 6.00 | 6.00 | 5.00 |
| Trp | 2.20 | 2.20 | 2.20 | 1.00 |
| Cys | — | – | — | 0.40 |

In the amino acid compositions of the present invention, the molar ratio of each amino acid may vary within ±30%, preferably ±20%, more preferably ±10% of the molar ratio of each amino acid in HVAAMA and HVAAMB in Table 2.

Test Example 2

(Effects to decrease exercise load during endurance exercise)

This test was conducted to confirm that the a administration of the amino acid composition of the present invention (HVAAM) before exercise decreased the exercise load during endurance exercise mice.

The experiments were conducted according to the method disclosed in Japanese Journal of Physical Fitness Sports Medicine,1995, 44:225–238. Namely, untrained mice (male; ddY), aged 5 weeks, 10 animals for each group, were fasted for 16 hours at room temperature and then orally administered a solution containing 1.8% (by weight) VAAM or HVAAMB in Table 2 at 37.5 $\mu$l per gram body weight. The mice were then allowed to rest for 30 minutes.

The mice were subjected to swimming exercise for 30 minutes in a river pool (a cylindrical water bath of 32 cm in diameter and 30 cm in depth) set at constant water flow rate of 8 m/min by a water circulation device and maintained at 35° C. After the swimming exercise, blood lactic acid, blood sugar (glucose) and blood free fatty acid in the mice were assayed. The results are shown in Tables 3, 4 and 5.

Figure 3:
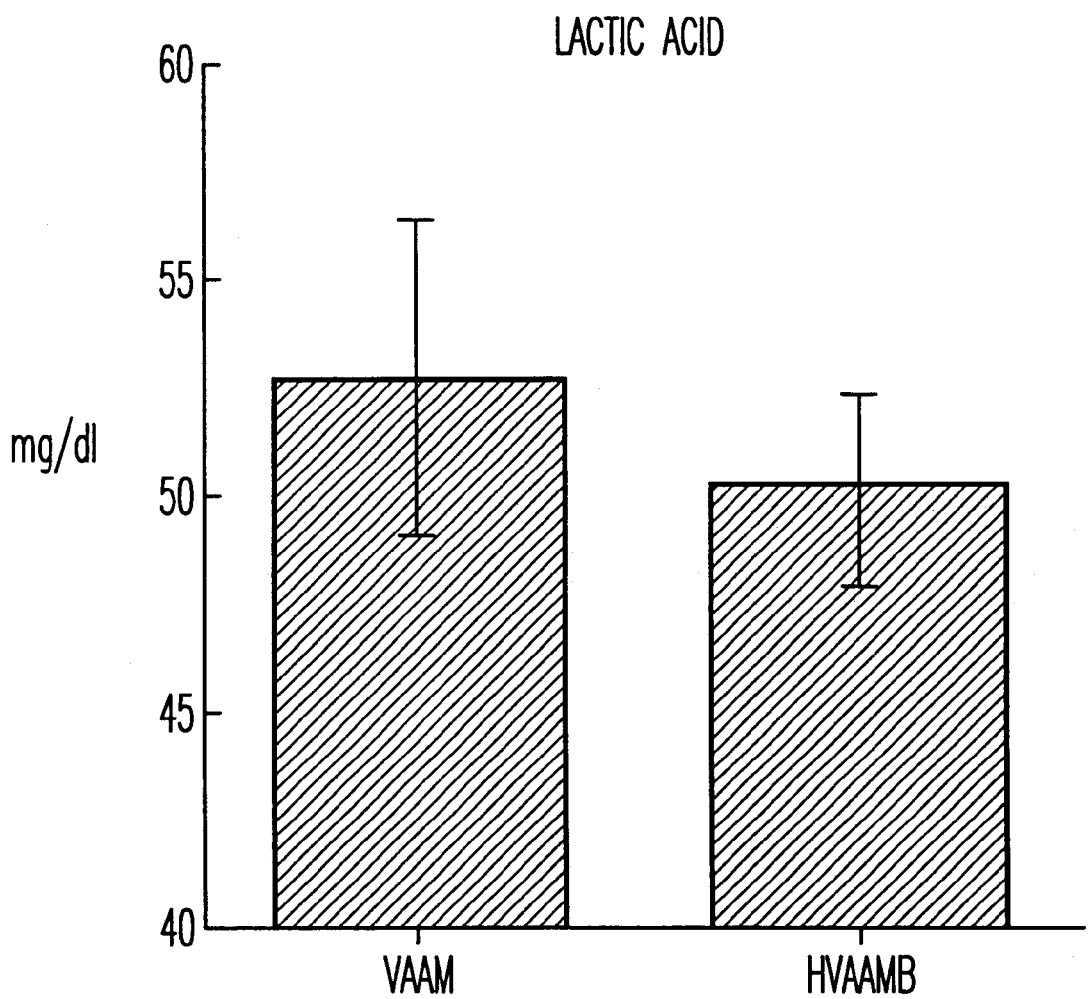
FIG. 3 is a graph which shows blood lactic acid levels (mean value) in the mice subjected to swimming after the administration of the composition of the present invention (HVAAM or VAAM). The vertical bars show standard deviation.
Figure 4:
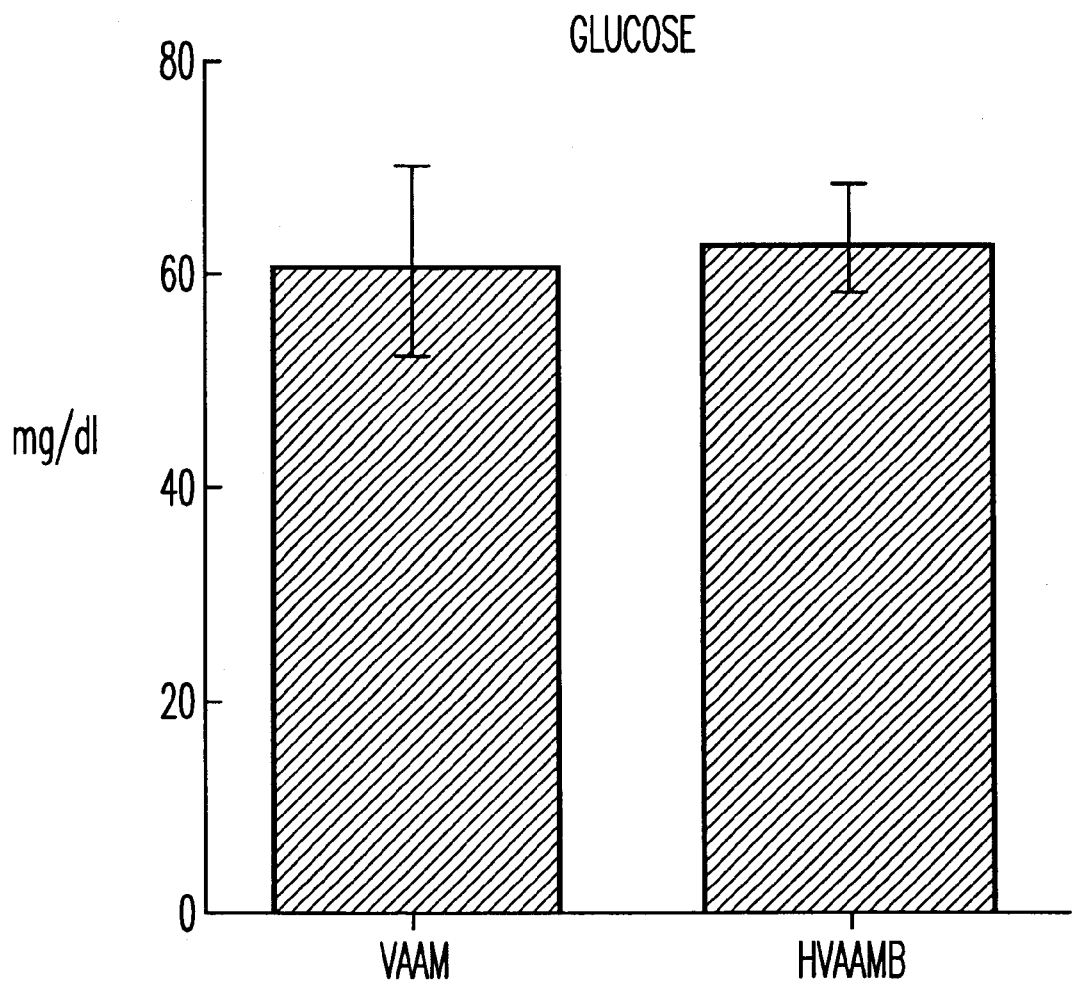
FIG. 4 is a graph which shows blood sugar (glucose) levels (mean value) in the mice subjected to swimming after the administration of the composition of the present invention (HVAAM or VAAM). The vertical bars show standard deviation.
Figure 5:
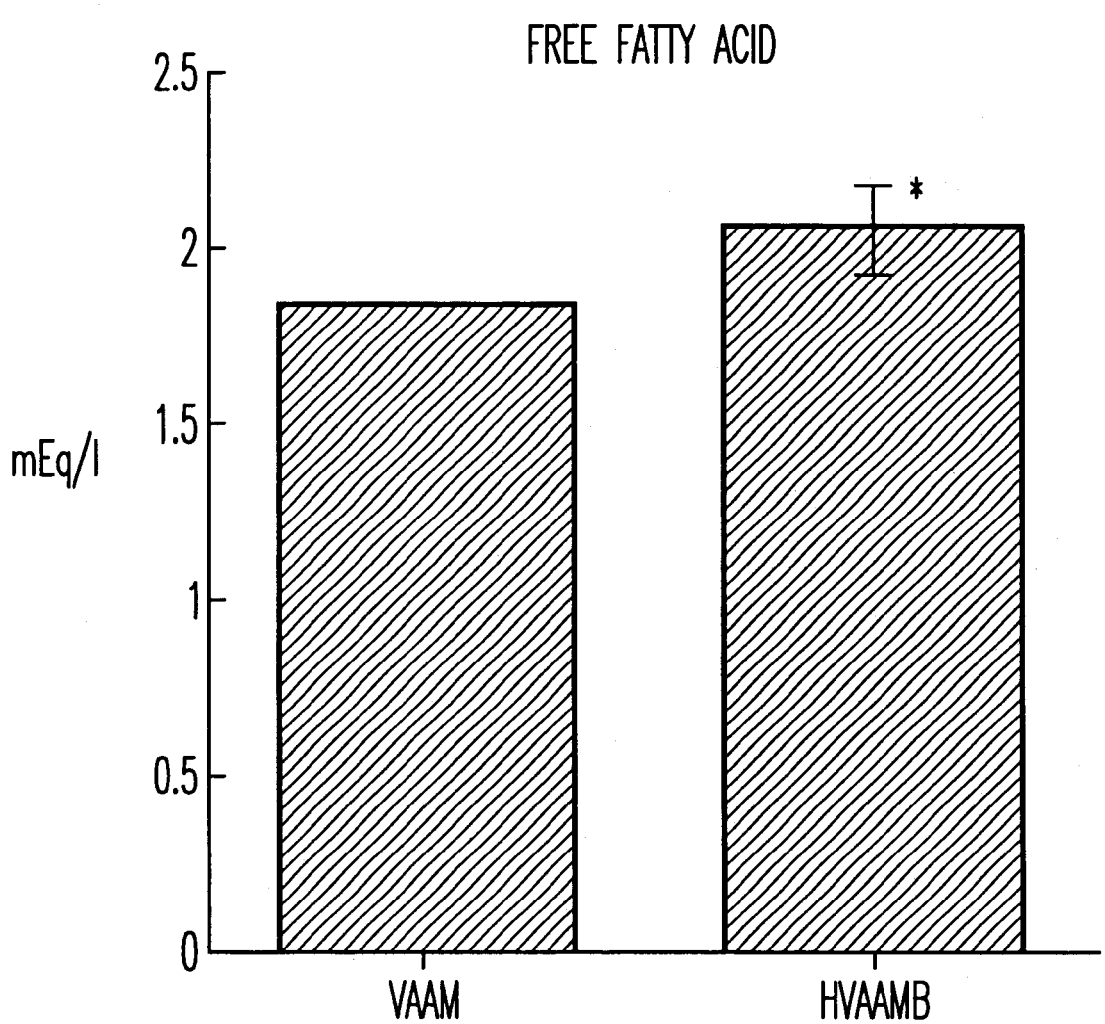
FIG. 5 is a graph which shows blood free fatty acid levels (mean value) in the mice subjected to swimming after the a administration of the composition of the present invention (HVAAM or VAAM). The vertical bars show standard deviation.

As compared with the VAAM administered nice, the HVAAMB administered mice showed lower blood lactic acid (FIG. 3), but higher blood sugar (FIG. 4) and higher blood free fatty acid (FIG. 5). The results show that the HVAAM decreases the exercise load caused by the exercise much more than the VAAM Test Example 3

(Effects of restraining the change in blood amino acid composition and keeping it constant)

This test was conducted to confirm that the administration of the amino acid composition of the present invention (HVAAM) before exercise restrained the decrease of blood amino acids during exercise on mice.

The experiments were conducted according to the method disclosed in Japanese Journal of Physical Fitness Sports Medicine, 1995, 44:225–238. Namely, untrained mice (male; ddY), aged 5 weeks, 10 animals for each group, were fasted for 16 hours at room temperature and then orally administered a solution containing 1.8% (by weight) HVAAMB in Table 2, CAAM (casein amino acid mixture) or glucose, or distilled water at 37.5 µl per gram body weight. The mice were then allowed to rest for 30 minutes.

The mice were subjected to swimming exercise for 30 minutes in the river pool. After the swimming exercise, the decrease in blood total amino acids in mice are shown in FIG. 6, and the change in blood amino acids for each nutrient administered group against the control group (distilled water administered group) is shown in FIG. 7.

Figure 6:
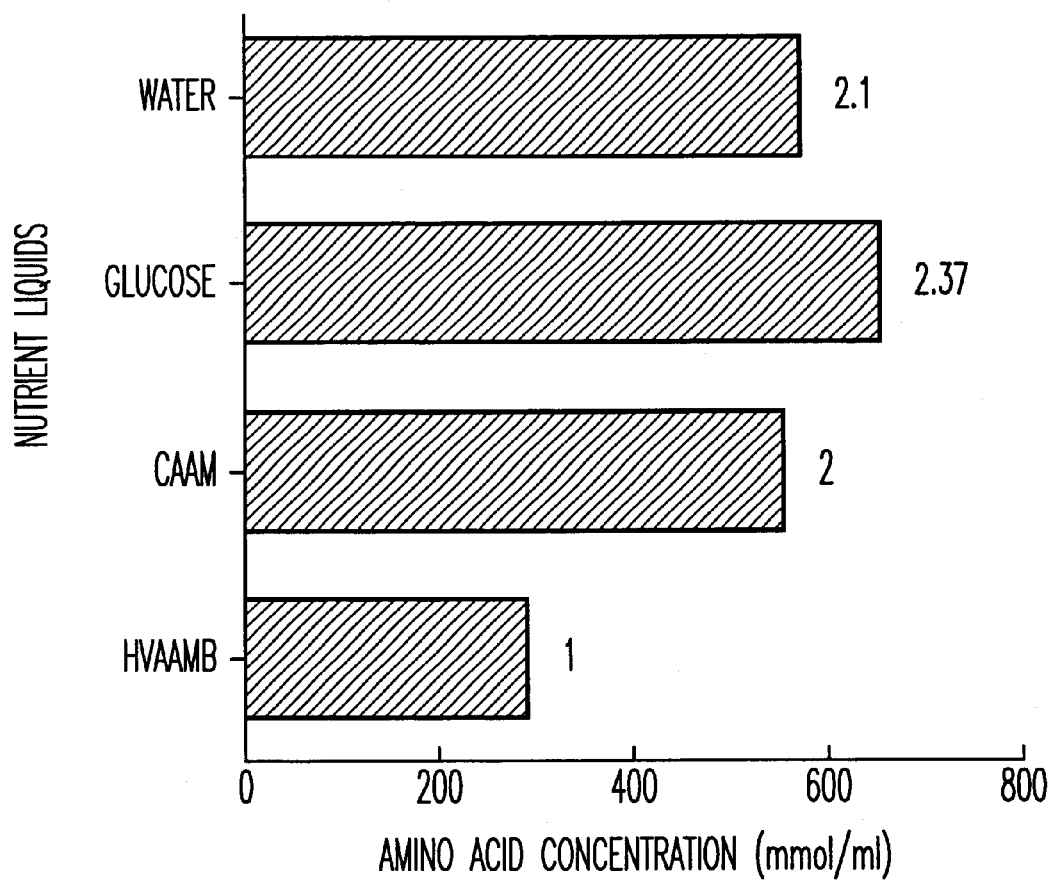
FIG. 6 is a graph which shows the decrease in blood amino acid levels (mean value) in the mice subjected to swimming after the administration of the composition of the present invention (HVAAM), CAAM, glucose or distilled water.

As shown in FIG. 6, the HVAAMB administered mice showed lower blood total amino acid levels, i.e., ½ of the CAAM administered mice, 1/2.37 of the glucose administered mice, and 1/2.1 of the water administered mice.

Figure 7:
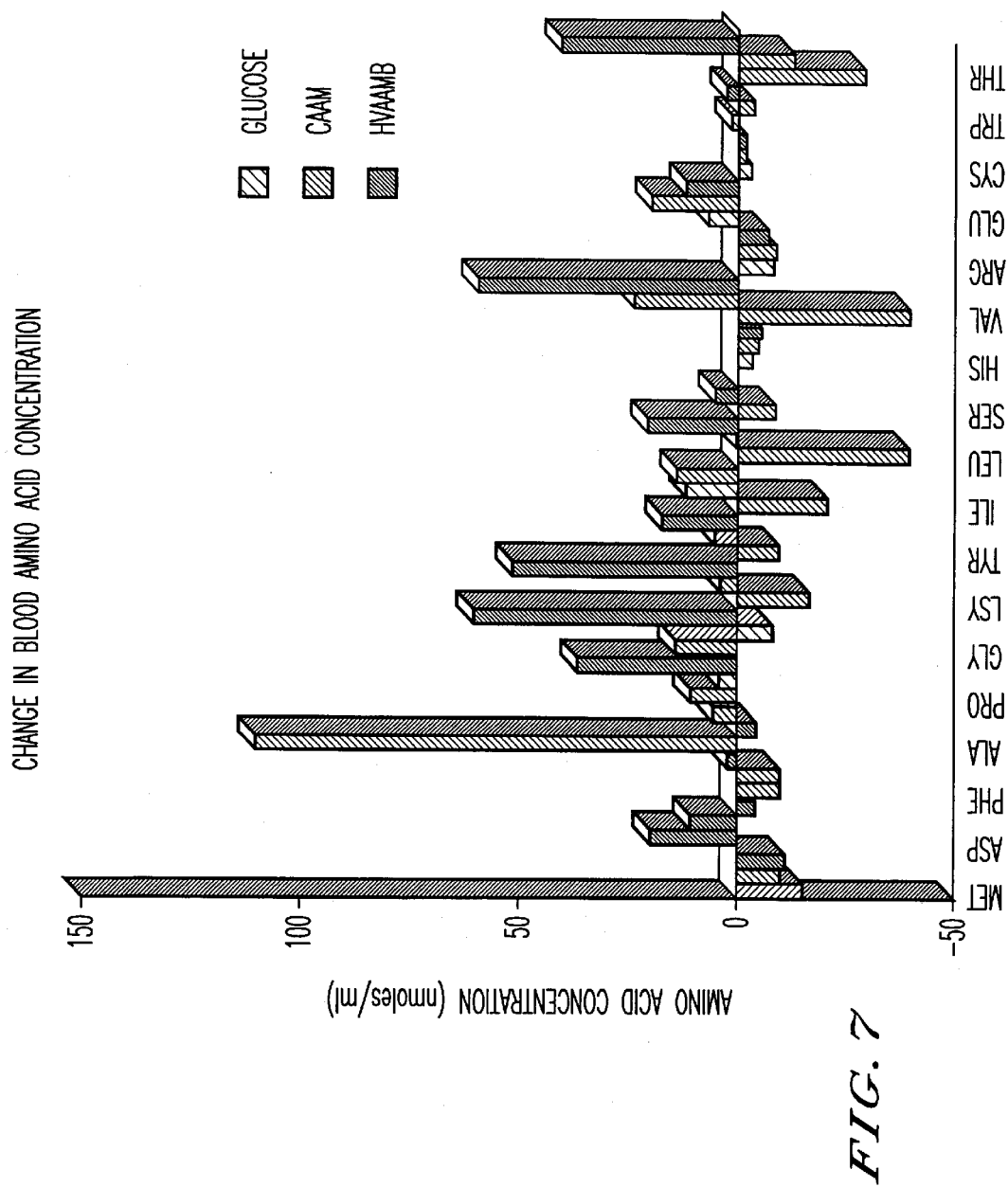
FIG. 7 is a graph which shows the change in blood amino acid levels (mean value) in the mice subjected to swimming after the administration of the composition of the present invention (HVAAM), CAAM, glucose or distilled water.

As seen from FIG. 7, the administration of the HVAAMB decreased slightly blood levels of arginine, histidine, methionine, and aspartic acid. However, it did not decrease so much blood levels of other amino acids, in particular, glycine, lysine, valine, glutamic acid and threonine as compared with the administration of CAAM or glucose. The results suggest that oxidation of fatty acid be promoted by the increase of blood non-esterified fatty acid concentration, which result in suppression of the use of the amino acids in TCA cycle.

Test Example 4

(Effects of restraining the change in blood amino acid composition and keeping it constant)

This test was conducted to confirm that the administration of the VAAM before exercise restrained the decrease of blood amino acid concentrations during exercise on rats.

Rats (Sprague Dawley rats; male)(aged 6 weeks and weighing 190 g (average), 8 animals for each group) were fasted for overnight and then orally administered 0.4 ml of a solution containing 3.8% by weight) VAAM in Table 2, or CAAM (casein amino acid mixture), or distilled water. The rats were then allowed to rest for 30 minutes at room temperature.

The rats were subjected to running exercise for 90 minutes on a motor-driven rodent treadmill with an incline of 7° at the rate of 23 m/min. Blood samples were taken just before the administration of the test liquid (−30 min), at the start (0 min), half-way through (45 min) and at the end (90 min) of running to determine lactic acid, glucose and no esterified fatty acid (NEFA). Another group of rats was treated with the same procedures except that they were not subjected to the running exercise. The results are shown in FIGS. 8 to 12.

Figure 8A:
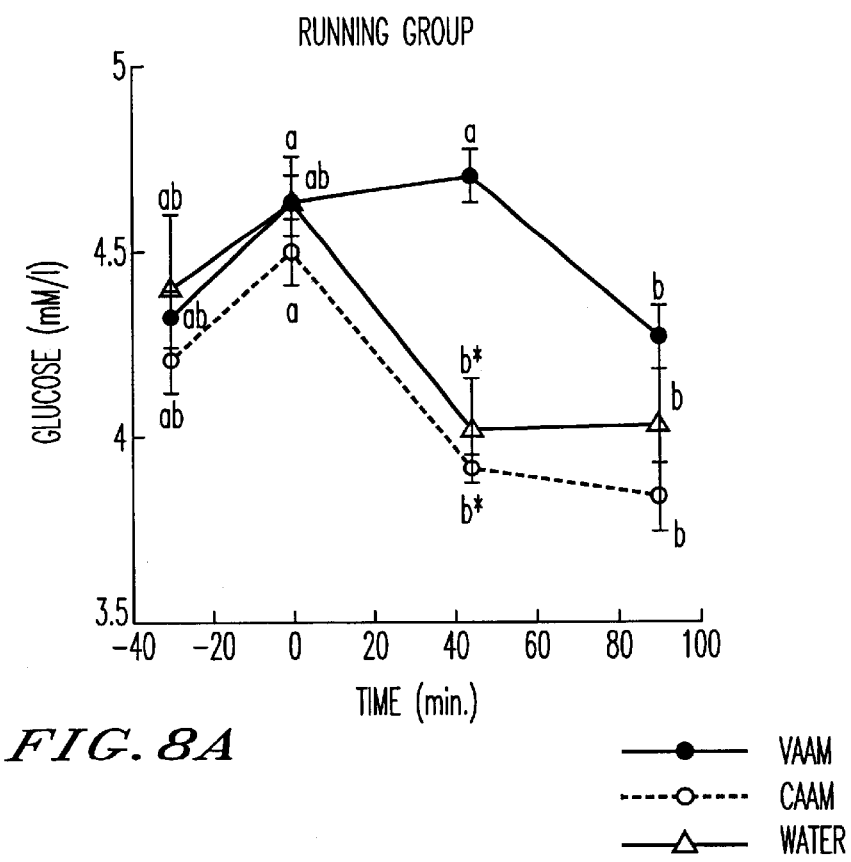
FIG. 8 is a graph which shows the change with time in blood glucose levels (mean value) in the rats subjected to running for a given time (a) or non-running (b) after the administration of the composition of the present invention (VAAM), CAAM or distilled water. The vertical bars show standard deviation.
Figure 8B:
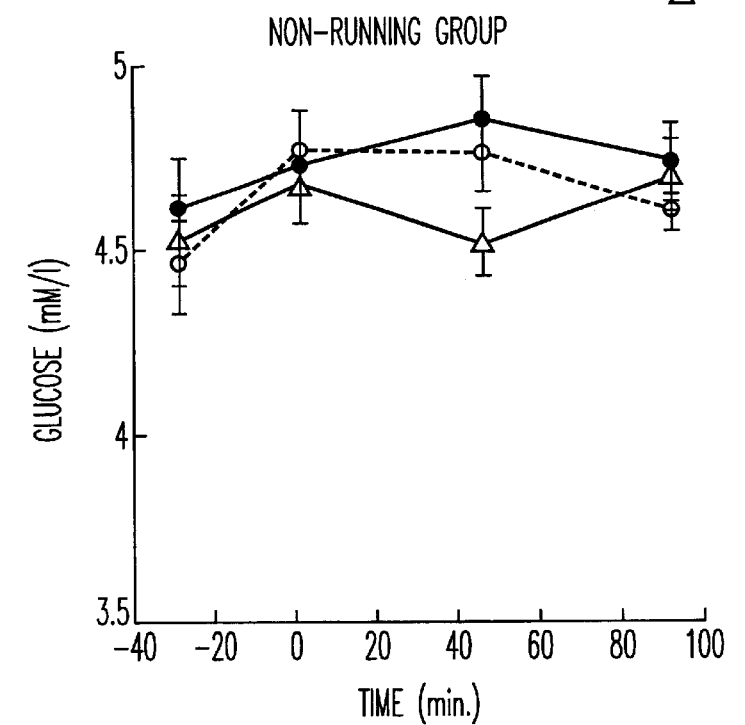
Figure 9A:
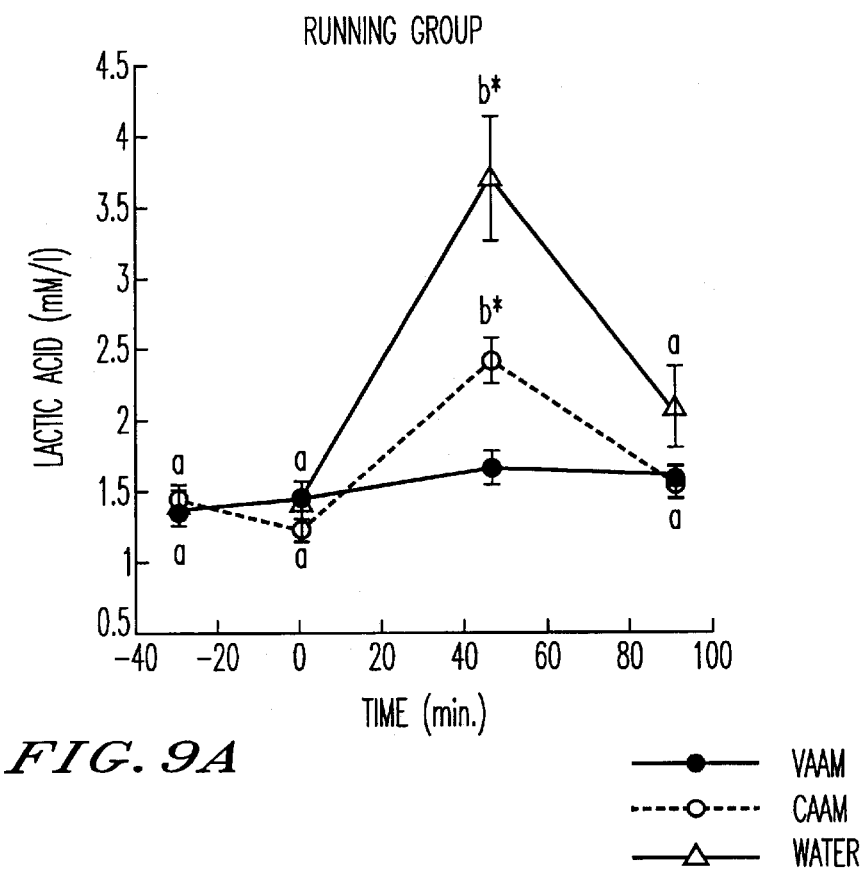
FIG. 9 is a graph which shows the change with time in blood lactic acid levels (mean value) in the rats subjected to running for a given time (a) or non-running (b) after the administration of the composition of the present invention (VAAM), CAAM or distilled water. The vertical bars show standard deviation.
Figure 9B:
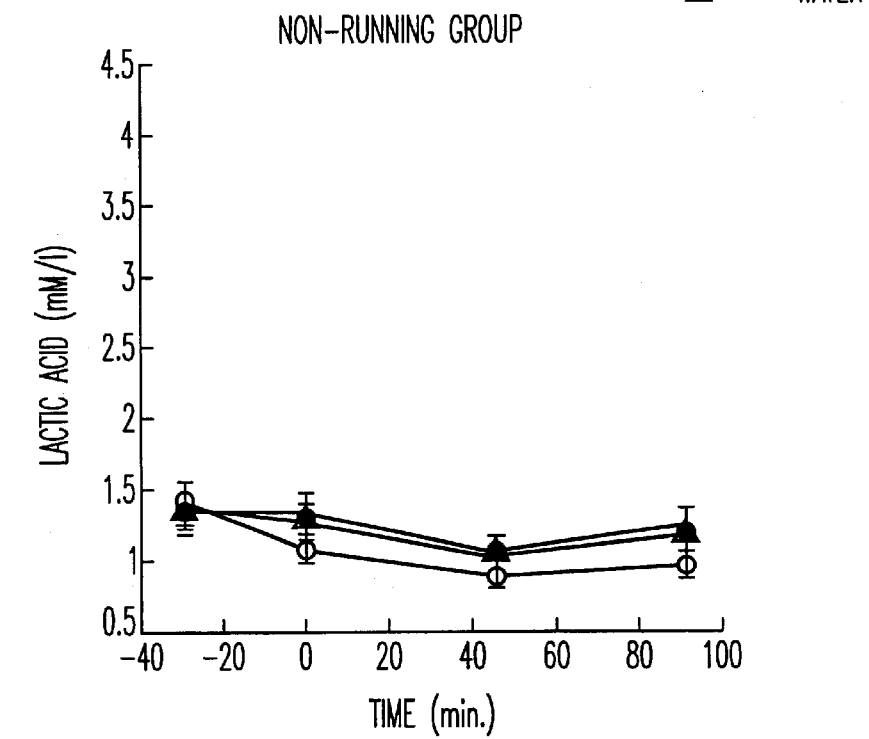
Figure 10A:
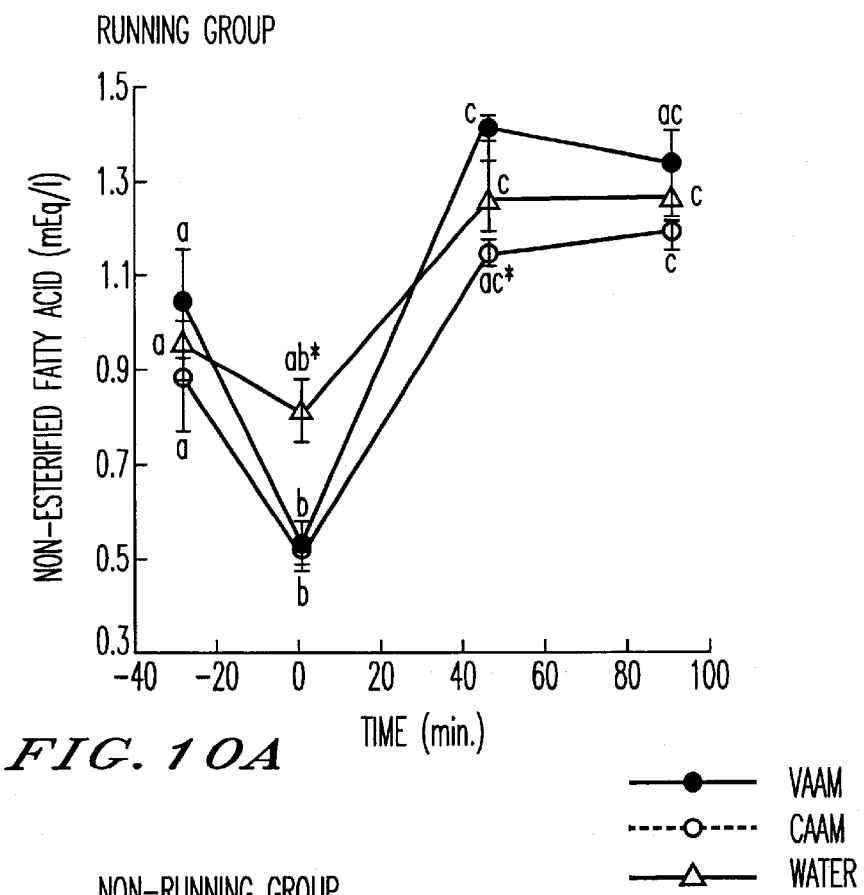
FIG. 10 is a graph which shows the change with time in blood non-esterified fatty acid levels (mean value) in the rats subjected to running for a given time (a) or non-running (b) after the administration of the composition of the present invention (VAAM), CAAM or distilled water. The vertical bars show standard deviation.
Figure 10B:
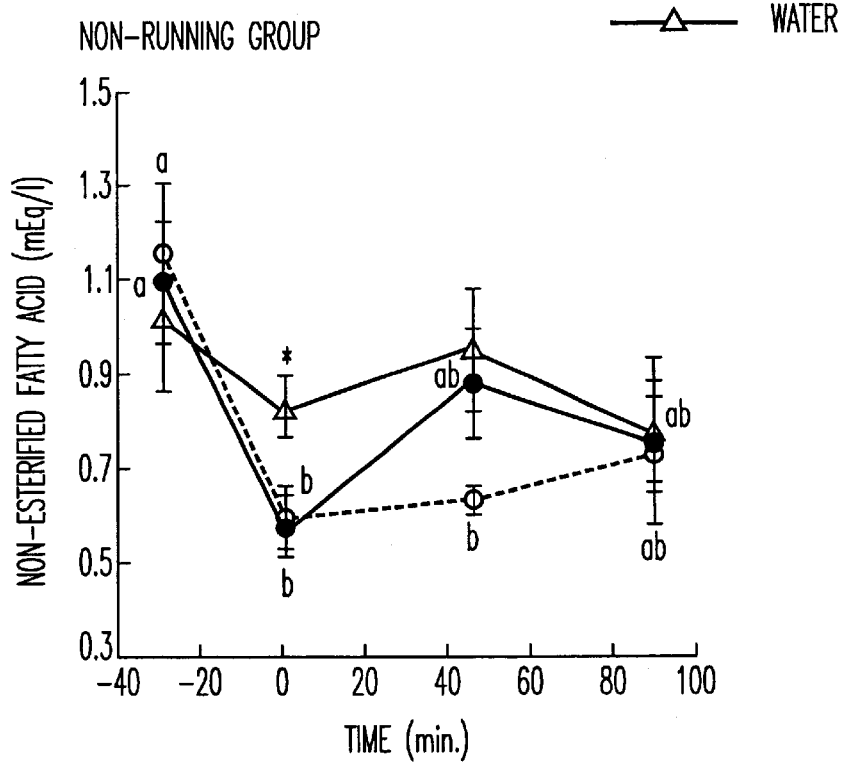

FIGS. 8 to 10 show the effects of the administration of the VAAM, CAAM or distilled water to rats on blood glucose levels, blood lactic acid levels and blood non-esterified fatty acid levels. FIGS. 8 to 10, (a) represents the running group, and (b) the non-running group. (*) represents significant difference ($p<0.05$) as compared with the VAAM administered group.

As seen from FIG. 8($a$), the blood glucose level in the CAAM and distilled water administered groups increased slightly, but then decreased significantly after 45 and 90 min of running exercise. In contrast, the blood glucose levels in the VAAM administered group did not fall after 45 min of running exercise and were significantly higher than those of the other groups ($p<0.05$) after 90 min of running. Any significant change ($p<0.05$) in blood glucose levels was not found in the non-running group (FIG. 8($b$)).

As seen from FIG. 9($a$), the blood lactic acid levels in the CAAM and distilled water administered groups increased significantly ($p<0.05$) after 45 min of running exercise but decreased after 90 min of running. In contrast, the blood lactic acid levels in the VAAM administered group did not significantly ($p<0.05$) change during the test. Any significant ($p<0.05$) change in blood lactic acid levels was not found in the non-running group (FIG. 9($b$)).

Further, as seen from FIG. 10, the blood non-esterified fatty acid levels decreased in all the groups before the administration (0 min) because of fasting but increased significantly ($p<0.05$) after 45 min of running exercise in the CAAM and VAAM administered groups with the VAAM group being significantly higher that the CAAM group. Any significant change in blood non-esterified fatty acid levels was not found in the non-running group (FIG. 10($b$)).

FIGS. 11 and 12 show the effects of the administration of the VAAM, CAAM or distilled water on blood amino acid levels in rats. In FIGS. 11 and 12, the black bar represents blood amino acid levels in the VAAM administered group, the striped bar those in the CAAM administered group and the white bar those in the distilled water administered group.

In FIG. 11 (the running group), (a) represents blood amino acid levels before the administration, (b) those after 30 min of the administration (0 min of running), (c) those after 45 min of running, and (d) those after 90 min of running. In FIG. 12 (the non-running group), (a) represents blood amino acid levels before the administration, (b) those after 30 min of the administration, (c) those after 45 min of the administration, and (d) those after 120 min of the administration. (*) represents significant difference ($p<0.05$) as compared with the VAAM administered group.

As seen from FIGS. 11($a$) and 12($a$), no significant difference in blood amino acid levels was found in the three groups before the administration of the test liquid.

Blood amino acid levels in the rats of the running group significantly increased after 30 min of the administration. But, the levels of glutamine, methionine and cystine in the VAAM administered group and cystine and glycine in the CAAM administered group did not increase FIG. 11($b$)).

The increase of blood amino acid levels in the rats of the non-running group after 30 min of the administration of the VAAM or CAAM are similar to that in the rats of the running group (FIG. 12($b$)).

Blood amino acid levels decreased after 45 min of running in all the groups except for tyrosine in the VAAM administered group (FIG. 11($c$)). The blood levels of glycine, alanine, valine, threonine, tyrosine, lysine and proline in the VAAM administered group were significantly higher than those of the water administered group. The blood levels of glycine, threonine, tyrosine and proline in the VAAM administered group were significantly higher than those of the CAAM administered group. The blood levels of valine and lysine in the CAAM administered group were significantly higher than those of the water administered group, but the blood levels of any amino acids in the CAAM administered group were not higher than those of the VAAM administered group.

In the non-running group, the levels of alanine and lysine did not increase in the VAAM administered group (FIG. 12($c$)). In the VAAM administered group, the level of tyrosine in the non-running group was lower than that in running group. However, in the CAAM or water administered group, the level of tyrosine in the running group was higher than that in the non-running group.

Figure 11A:
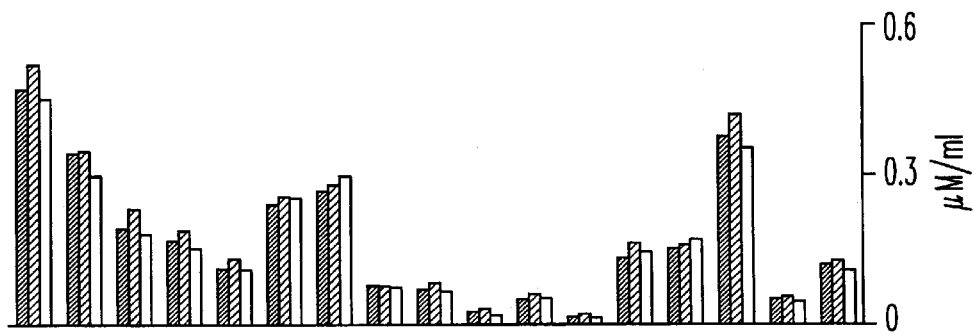
FIG. 11 is a graph which shows the change with time in blood amino acid levels in the rats subjected to running for a given time after the administration of the composition of the present invention (VAAM), CAAM or distilled water. The black bars show blood amino acid levels in the VAAM administered group, the striped bars those in the CAAM administered group and the white bars those in he distilled water administered group. The composition of blood amino as is presented for (a) before the administration, (b) 30 minutes after the administration (just before running), (c) after running for 45 minutes and (d) after running for 90 minutes. The signal (*) shows significant difference compared with the VAAM administered group ($p<0.05$).
Figure 11B:
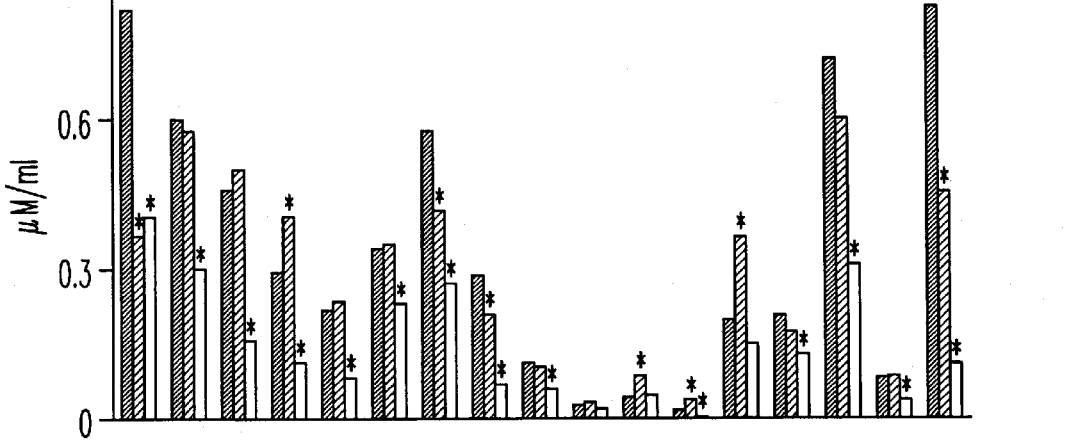
Figure 11C:
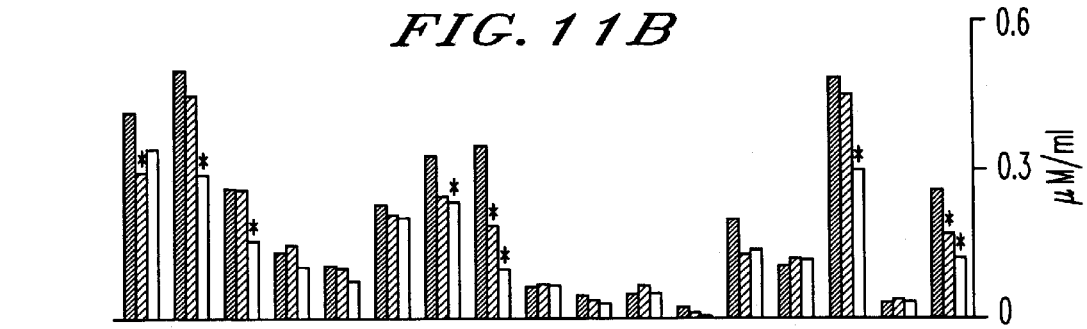
Figure 11D:
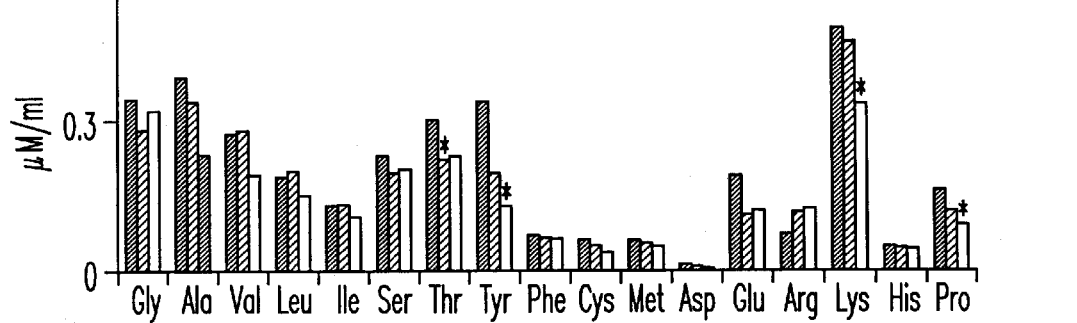
Figure 12A:
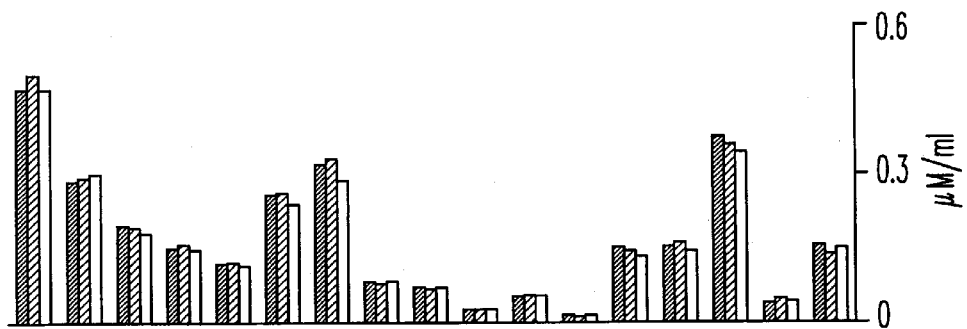
FIG. 12 is a graph which shows the change with time in blood amino acid levels in the rats not subjected to running for a given time after the administration of the composition of the present invention (VAAM), CAAM or distilled water. The black bars show blood amino acid levels in the VAAM administered group, the striped bars those in the CAAM administered group and the white bars those in the distilled water administered group. The composition of blood amino acids is presented for (a) before the administration, (b) 30 minutes after the administration, (c) 75 minutes after the administration and (d) 120 minutes after the administration. The signal (*) shows significant difference compared with the VAAM administered group ($p<0.05$).
Figure 12B:
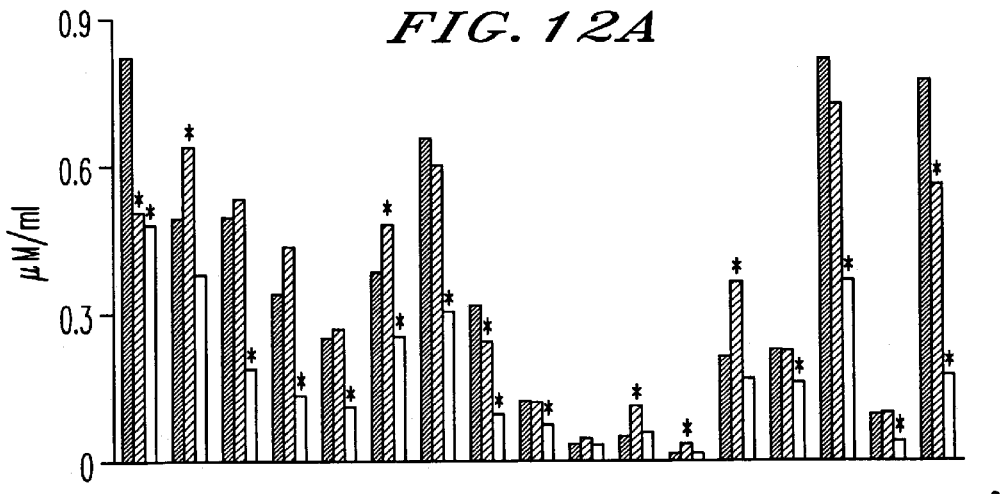
Figure 12C:
Figure 12D:
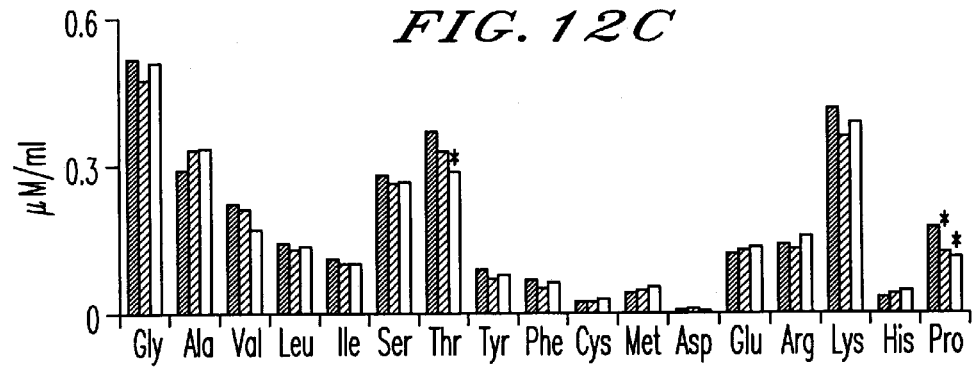

At the end of the running, the levels of valine, leucine, serine, threonine, tyrosine and lysine in the VAAM administered group decreased little as compared with those after 45 min of running (FIG. 11(d)). The levels of threonine, tyrosine, lysine and proline in the VAAM administered group were significantly higher than those after 90 of running in the water administered group In the non-running group, the levels of threonine and proline in the VAAM administered group were higher than those in the running group after 120 min of the administration of distilled water.

The above results show that the administration of the VAAM restrains the consumption of amino acids caused by exercise and therefore the VAAM can restrain the induction of fatigue by exercise.

Industrial applicability

The amino acid composition of the present invention supplements blood amino acids reduced during hard exercise and shows effects to improve motor function, to reduce fatigue after exercise and to help recovery from the fatigue. The administration of the composition of the present invention restrains the consumption of amino acids caused by exercise and the induction of fatigue by exercise.

What is claimed is:

1. An amino acid composition comprising the following amino acids at the following molar ratio:

| | |
|---|---|
| proline | 12.6 to 23.4 moles |
| alanine | 8.4 to 15.6 moles |
| glycine | 13.3 to 24.9 moles |
| valine | 8.2 to 15.4 moles |
| threonine | 5.0 to 9.4 moles |
| leucine | 4.3 to 8.1 moles |
| histidine | 1.8 to 11.9 moles |
| serine | 1.7 to 3.3 moles |
| lysine | 6.0 to 11.2 moles |
| isoleucine | 3.1 to 5.9 moles |
| glutamic acid | 2.2 to 10.4 moles |
| arginine | 2.4 to 4.6 moles |
| phenylalanine | 2.6 to 5.0 moles |
| tyrosine | 4.2 to 7.8 moles |
| and | |
| tryptophan | 1.5 to 2.9 moles. |

2. The amino acid composition of claim 1 comprising the following amino acids at the following molar ratio:

| | |
|---|---|
| proline | 14.4 to 21.6 moles |
| alanine | 9.6 to 14.4 moles |
| glycine | 15.2 to 23.0 moles |
| valine | 9.4 to 14.2 moles |
| threonine | 5.8 to 8.7 moles |
| leucine | 5.0 to 7.5 moles |
| histidine | 2.0 to 11.0 moles |
| serine | 2.0 to 3.0 moles |
| lysine | 6.8 to 10.4 moles |
| isoleucine | 3.6 to 5.4 moles |
| glutamic acid | 2.5 to 9.6 moles |
| arginine | 2.8 to 4.2 moles |
| phenylalanine | 3.0 to 4.6 moles |
| tyrosine | 4.6 to 7.2 moles |
| and | |
| tryptophan | 1.7 to 2.7 moles. |

3. The amino acid composition of claim 1 comprising the following amino acids at the following molar ratio:

| | |
|---|---|
| proline | 16.2 to 19.8 moles |
| alanine | 10.8 to 13.2 moles |
| glycine | 17.1 to 21.1 moles |
| valine | 10.6 to 13.0 moles |
| threonine | 6.4 to 8.0 moles |
| leucine | 5.5 to 6.8 moles |
| histidine | 2.3 to 10.1 moles |
| serine | 2.2 to 2.8 moles |
| lysine | 7.7 to 9.5 moles |
| isoleucine | 4.0 to 5.0 moles |
| glutamic acid | 2.8 to 8.8 moles |
| arginine | 3.1 to 3.9 moles |
| phenylalanine | 3.4 to 4.2 moles |
| tyrosine | 5.4 to 6.6 moles |
| and | |
| tryptophan | 1.9 to 2.5 moles. |

4. The amino acid composition of claim 1 wherein the molar ratio of histidine is 6.4 to 11.9 moles and that of glutamic acid is 5.6 to 10.4 moles.

5. A supplementary liquid which comprises the amino acid composition as defined in any one of claims 1 to 4.

6. A food which comprises the amino acid composition of any one of claims 1 to 4.

7. A beverage which comprises the amino acid composition of any one of claims 1 to 4.

8. A medicine which comprises the amino acid composition of any one of claims 1 to 4.

* * * * *

UNITED STATES PATENT AND TRADEMARK OFFICE
CERTIFICATE OF CORRECTION

PATENT NO. : 6,224,861 B1
DATED : May 1, 2001
INVENTOR(S) : Takashi Abe et al.

It is certified that error appears in the above-identified patent and that said Letters Patent is hereby corrected as shown below:

<u>Title page,</u>
Item [57], line 4, "eucine" should read -- leucine --;
Line 8, "trypsin" should read -- tryptophan --.

<u>Column 1,</u>
Line 42, "bee" should read -- been --.

<u>Column 2,</u>
Line 13, "add" should read -- acid --;
Lines 32 and 65, "trypsin" should read -- tryptophan --.

<u>Column 4,</u>
Line 54, "trypsin" should read -- tryptophan --.

<u>Column 5,</u>
Line 9, "trypsin" should read -- tryptophan --;
Line 21, "a no" should read -- amino --;
Line 31, "-methyl" should read -- 3-methyl --.

<u>Column 6,</u>
Line 14, "100 1 400 ml," should read -- 100 to 400 ml, --;
Line 18, "d tail" should read -- detail --.

<u>Column 7,</u>
Line 3, "a ids" should read -- acids --;
Line 53, "ammo" should read -- amino --.

UNITED STATES PATENT AND TRADEMARK OFFICE
CERTIFICATE OF CORRECTION

PATENT NO. : 6,224,861 B1
DATED : May 1, 2001
INVENTOR(S) : Takashi Abe et al.

It is certified that error appears in the above-identified patent and that said Letters Patent is hereby corrected as shown below:

Column 8,
Line 51, "nice," should read -- mice, --.

Signed and Sealed this

Twenty-sixth Day of February, 2002

Attest:

Attesting Officer

JAMES E. ROGAN
Director of the United States Patent and Trademark Office